United States Patent
Mo et al.

(10) Patent No.: US 9,884,795 B2
(45) Date of Patent: Feb. 6, 2018

(54) QUINONE COMPOUNDS FOR INHIBITING MONOMER POLYMERIZATION

(71) Applicant: BAKER HUGHES INCORPORATED, Houston, TX (US)

(72) Inventors: Hua Mo, Friendswood, TX (US); Roger D. Metzler, Sugar Land, TX (US)

(73) Assignee: Baker Hughes, a GE company, LLC, Houston, TX (US)

( * ) Notice: Subject to any disclaimer, the term of this patent is extended or adjusted under 35 U.S.C. 154(b) by 0 days.

(21) Appl. No.: 15/437,227

(22) Filed: Feb. 20, 2017

(65) Prior Publication Data

US 2017/0158584 A1 Jun. 8, 2017

Related U.S. Application Data

(62) Division of application No. 13/660,488, filed on Oct. 25, 2012, now Pat. No. 9,611,336.

(51) Int. Cl.
| | | |
|---|---|---|
| C07C 50/02 | (2006.01) | |
| C07C 7/20 | (2006.01) | |
| C09K 15/08 | (2006.01) | |

(52) U.S. Cl.
CPC ............. *C07C 7/20* (2013.01); *C09K 15/08* (2013.01)

(58) Field of Classification Search
None
See application file for complete search history.

(56) References Cited

U.S. PATENT DOCUMENTS

| | | | |
|---|---|---|---|
| 4,032,547 A | 6/1977 | Bacha et al. | |
| 4,590,301 A | 5/1986 | Lim et al. | |
| 5,128,022 A | 7/1992 | Reid | |
| 5,562,863 A | 10/1996 | Arhancet | |
| 5,616,774 A | 4/1997 | Evans et al. | |
| 6,184,276 B1 | 2/2001 | Ignatz-Hoover | |
| 6,284,936 B2 | 9/2001 | Shahid | |
| 6,447,649 B1 | 9/2002 | Arhancet | |
| 6,685,823 B2 | 2/2004 | Benage et al. | |
| 6,926,820 B2 | 8/2005 | Eldin et al. | |
| 7,651,635 B1 | 1/2010 | Lewis | |
| 7,943,809 B2 | 5/2011 | Benage et al. | |
| 2002/0037958 A1* | 3/2002 | Benage | C07B 63/04 524/714 |
| 2009/0287013 A1 | 11/2009 | Morrison et al. | |
| 2012/0101295 A1 | 4/2012 | Weyler et al. | |
| 2014/0194559 A1 | 7/2014 | Price et al. | |

FOREIGN PATENT DOCUMENTS

| | | |
|---|---|---|
| JP | 3 197430 B2 | 8/2001 |
| WO | 2012033800 A1 | 3/2012 |

OTHER PUBLICATIONS

European Search Report in Appln 13849430.7, dated Jun. 15, 2016.
Engel, Paul S., et al., "The reaction of a-phenethyl radicals with 1,4-benzoquinone and 2,6-di-tert-butyl-1,4-benzoquinone", Tetrahedron 66, 8805-8814, 2010.
Mo, Hua, "Benzylic Radical Scavenging Process by Quinoid Inhibitors", Dissertation, Rich Univerisiy, 2004.
Chesnokov et al., "Influence of o-benzoquinone nature on initiation of radical polymerization by the obenzoquinone-tert-amine system," Russian Chemical Bulletin, Intl. Ed. vol. 50, No. 12, pp. 2366-2371 (2001).
Braun, Macromol., Symp. 1996, 111, 63-71.
Shushunova, et al., Polymer Science, Ser. B, 2009, vol. 51, 427-437.

\* cited by examiner

*Primary Examiner* — Clinton A Brooks
*Assistant Examiner* — Ana Z Muresan
(74) *Attorney, Agent, or Firm* — Mossman, Kumar & Tyler, P.C

(57) ABSTRACT

The polymerization of monomers may be at least partially reduced or inhibited by introducing an effective amount of an additive. The additive may be or include a first compound:

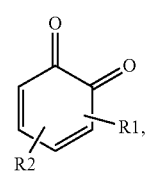

where:
R1 and R2 may be or include an alkyl group, an aryl group, an alkyl group having a heteroatom, an aryl group having a heteroatom, and combinations thereof. The hetero atom may be or include sulfur, nitrogen and/or oxygen. R1 may be the same or different from R2. The polymerizable monomers may be or include, but are not limited to styrene, butadiene, isoprene, acrylic acid, acrylonitrile, vinyl acetate, and combinations thereof.

3 Claims, 2 Drawing Sheets

QUINONE COMPOUNDS FOR INHIBITING MONOMER POLYMERIZATION

CROSS-REFERENCES TO RELATED APPLICATIONS

This application is a divisional application of U.S. patent Ser. No. 13/660,488 filed on Oct. 25, 2012.

TECHNICAL FIELD

The present invention relates to reducing or inhibiting the polymerization of monomers, and more specifically relates to introducing to the monomers an effective amount of an additive to inhibit their polymerization.

BACKGROUND

Common industrial methods for producing various compounds containing vinyl functionality such as styrene, ethene, butadiene, isoprene, vinyl acetate, (meth)acrylic acid, (meth)acrylates, acrolein, acrylonitrile or vinyl-substituted aromatics, typically include separation and purification processes such as distillation to remove unwanted impurities or byproducts. However, undesired polymerization, especially during monomer purification processes such as distillation, results in loss of the monomer product. Moreover, loss of production due to polymer formation on process equipment continues to cause operating problems for those in the industry. In particular, plugging of distillation column overhead piping and fouling or plugging of condensers has been problematic. Therefore, the industry has sought compositions and methods that are less dangerous to handle, that are effective in multiple phases, and that reduce product losses and production problems.

Consequently, additives, which are referred to either as polymerization inhibitors or as polymerization retarders, are added to the olefinically unsaturated monomers generally as early as during the preparation process. Polymerization inhibitors are, as the name actually states, capable of effectively preventing undesired polymerization. Since the reaction rate of polymerization inhibitors is fast, polymerization inhibitors are consumed within a short time. The polymer content rises quickly thereafter. Polymerization retarders, in contrast, can partially prevent polymerization. The rate of polymerization slowly increases Therefore polymerization is effectively hindered or inhibited for a longer period of time, e.g. 4 hours. Due to slow reaction rate, polymerization retarder consumes significantly more slowly than polymerization inhibitors. In general, polymerization inhibitors are used to inhibit polymerization under normal process conditions; whereas, polymerization retarders are used to decrease polymerization reactions during an abnormal process condition, such as an emergency shutdown. The presence of both polymerization inhibitors and polymerization retarders in monomer production may be justified.

It is well known that undesirable and costly polymerization is a significant problem during the manufacturing of various vinyl monomers, particularly vinyl aromatic compounds (e.g., styrene, alpha-methylstyrene and vinyltoluene). Many kinds of polymerization inhibitors and polymerization retarders have been used in the past to minimize this problem. Examples of polymerization inhibitors that have been used to control polymer formation include alkyl-substituted di-nitro-phenols and nitrosophenols diethylhydroxylamine, phenyl-p-phenylenediamines, tert-butyl catechol, and phenothiazine. However, many of these compounds are difficult to handle, are expensive, and/or are regulated heavily with regards to their environmental effect.

Thus, it would be desirable if new polymerization retarders could be developed to inhibit and/or at least partially inhibit the rate of monomer polymerization and which are also cost effective.

SUMMARY

There is provided, in one form, a method for inhibiting the polymerization of monomers by introducing an effective amount of an additive to at least partially inhibit their polymerization. The additive may be or include a first compound:

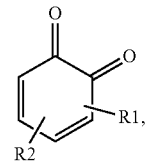

(A)

where:
R1 and R2 may be or include an alkyl group, an aryl group, an alkyl group, an alkyl group having a heteroatom, an aryl group having a heteroatom, and combinations thereof. The hetero atom may be or include, but is not limited to sulfur, nitrogen, oxygen, and combinations thereof. Non-limiting examples may be or include an ether group, a thiol group, and/or an ester group. R1 may be the same or different from R2.

There is further provided in another non-limiting embodiment, a method for at least partially inhibiting the polymerization of monomers by introducing an effective amount of an additive to the monomers. The additive may be or include a polymerization retarder, such as 3,5-di-tert-butyl-1,2-benzoquinone (3,5 BQ); 2,5-di-tert-butyl-1,4-benzoquinone (2,5 BQ); and combinations thereof.

In an alternative embodiment, a treated monomer stream is provided. The treated monomer stream may include, but is not limited to, polymerizable monomers, and an additive therein for at least partially inhibiting the polymerization of the monomers within the monomer stream. The additive may be or include a first compound of the general formula:

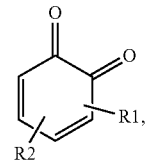

(A)

and
where R1 and R2 may be or include an alkyl group, an aryl group, an alkyl group having a heteroatom, an aryl group having a heteroatom, and combinations thereof. The hetero atom may be or include, but is not limited to sulfur, nitrogen, oxygen, and combinations thereof. R1 may be the same or different from R2.

The additive appears to at least partially inhibit the polymerization of the polymerizable monomers over a period of time.

DETAILED DESCRIPTION

Figure 1:
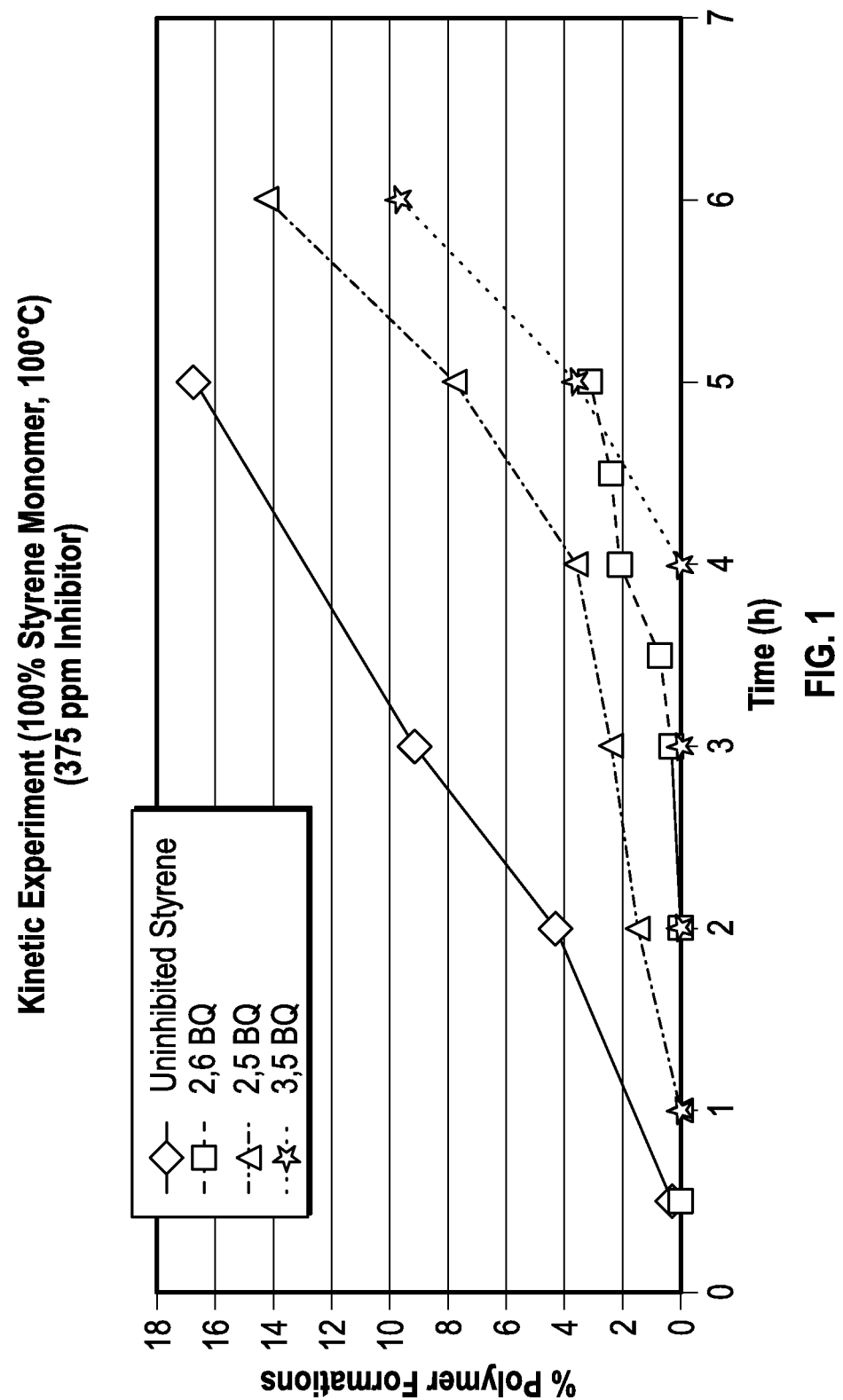
FIG. 1 is a graph illustrating the percent polymer formation compared to the amount of time each polymerization retarder is present.

It has been discovered that the polymerization of monomers may be at least partially reduced or inhibited by introducing to the monomers an effective amount of an additive. The monomer may be or include, but is not limited to acrylic monomers and/or vinyl monomers; alternatively, the monomers may be or include, but are not limited to styrene, butadiene, isoprene, acrylic acid, vinyl acetate, acrylonitrile, and combinations thereof. Non-limiting examples of where the polymerization of the monomers tends to be problematic include, but are not limited to light ends, a primary fractionator, pyrolysis gas, and the like. The additive may include at least one polymerization retarder, a polymerization inhibitor, and combinations thereof. Prevent or inhibit is defined herein to mean that the additive may suppress or reduce the amount of total polymerization. That is, it is not necessary for the polymerization to be entirely prevented for the methods and compositions discussed herein to be considered effective, although complete prevention is a desirable goal.

The additive may be or include a first compound, such as but not limited to compound (A) of the general formula:

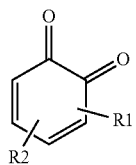

(A)

R1 and R2 may be or include an alkyl group, an aryl group, an alkyl group having a heteroatom, an aryl group having a heteroatom, and combinations thereof. The heteroatom may be or include but is not limited to sulfur, nitrogen, oxygen, and combinations thereof. Non-limiting examples may be or include an ether group, a thiol group, and/or an ester group. The alkyl group of R1 and/or R2 may have from 1 C atom independently to 50 C atoms; alternatively from about 1 C independently to about 20 C atoms. R1 may be the same or different from R2. In one non-limiting embodiment, compound (A) may be 3,5-di-tert-butyl-1,2-benzoquinone (3,5 BQ), 3,5-di-methyl-1,2-benzoquinone, 3,6-di-tert-butyl-1,2-benzoquinone and combinations thereof.

In a non-limiting embodiment, the additive may include a second compound, such as but not limited to 2,6-di-tert-butyl-1,4-benzoquinone (2,6 BQ); 2,5-di-tert-butyl-1,4-benzoquinone (2,5 BQ); 4-sec-butyl-2,6-di-tert-butylphenol; and combinations thereof. The second compound may be used alone, or in combination with the first compound, such that the ratio between the first compound and the second compound within the additive is based on weight and may range from about a 1:1 ratio independently to about a 1:5 ratio, alternatively from about a 1:1 ratio independently to about a 1:3 ratio. The first compound, i.e. compounds of the formula (A), and the second compound are classified as 'polymerization retarders' for purposes of the methods described. As used herein with respect to a range, "independently" means that any lower threshold may be used together with any upper threshold to give a suitable alternative range.

The first compound and/or the second compound, i.e. polymerization retarders, may at least partially inhibit or reduce the rate of polymerization of the monomers for about 0.25 hours independently to about 4 hours at 375 ppm, alternatively from about 0.25 hours independently to about 3 hours, or from about 0.5 hours independently to about 2 hours. 'First compound' and 'second compound' are used herein to differentiate between the two types of compounds. The terms 'first' and 'second' are used in this context as descriptors and are not meant to limit the compounds to a particular order of use; these compounds may be added to the monomers in any order. Said differently, the 'first compound' may be added after the 'second compound', and vice versa.

The methods described are considered successful if the additive inhibits more of the monomer polymerization than would occur in the absence of the additive. Alternatively, success is obtained if a majority of the monomer polymerization is at least partially inhibited, from about 90% independently to about 99.9%, or from about 96% independently to about 99% in another non-limiting embodiment.

The additive may include a known polymerization inhibitor, such as but not limited to a nitroxide, a hydroxylamine, quinone methide, phenylenediamine derivatives, a hindered phenol, and combinations thereof. The nitroxide may be or include 2,2,6,6-tetramethyl-1-piperidinyloxyl (TEMPO); 4-OXOTEMPO; 1-oxyl-2,2,6,6-tetramethylpiperidine; 1-oxyl-2,2,6,6-tetramethypiperidin-4-one; 1-oxyl-2,2,6,6-tetramethylpiperidin-4-yl-2-acetate; 1-oxy1-2,2,6,6tetramethyl-1-piperidin-4-yl-2-ethylhexanoate; and combinations thereof.

The hydroxylamine may be or include hydroxylamines substituted with at least one alkyl, aryl or alkylaryl group include, but are not necessarily limited to N-ethylhydroxylamine (EHA); N,N'diethylhydroxylamine (DEHA); N-ethyl-N-35 methylhydroxylamine (EMHA); N-isopropylhydroxylamine (IPHA); N,N'dibutylhydroxylamine (DBHA); N-amylhydroxylamine (AHA); N-phenylhydroxylamine (PHA); and combinations thereof.

The phenylene diamine may be substituted with at least one alkyl group, aryl group, alkylaryl group, and combinations thereof. Non-limiting examples of phenylenediamine derivatives that may be used include, but are not limited to N,N'-Di-sec-butyl-p-phenylenediamine, N,N'-Di-phenyl-p-phenylenediamine, N,N-Dimethyl-p-phenylenediamine, N-phenyl-p-phenylenediamine, and combinations thereof.

Compound (1) has the general formula:

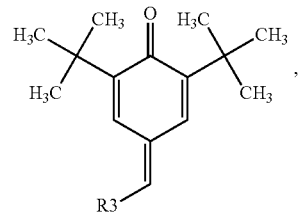

and where R3 may be or include an alkyl group, an aryl group, an alkyl group having a heteroatom, an aryl group having a heteroatom, and combinations thereof. The heteroatom may be or include, but is not limited to sulfur, nitrogen, oxygen, and combinations thereof.

The polymerization inhibitor may be used in conjunction with either the first compound, or the polymerization inhibitor may be part of an additive that includes the first compound and the second compound. When the first compound and/or the second compound are combined with the polymerization inhibitor, the polymerization of the monomers may be at least temporarily and/or partially inhibited in another non-limiting embodiment. The ratio between the polymerization retarder(s); i.e. either the first compound, or the combination of the first compound and the second compound; and the polymerization inhibitor may be based on weight and range from about 1:1 to about 1:10, alternatively from about 1:1 independently to about 1:5.

The additive may be dispersed in a suitable liquid carrier dispersing medium or alkyl and aromatic solvent, such as but not limited to, heavy aromatic naptha, ethylbenzene, xylene, styrene, paraffinic solvent, and combinations thereof. The amount of the solvent used with the additive may have a ratio based on weight ranging from about a 100:1 ratio independently to about a 2:1 ratio, alternatively from about a 20:1 ratio independently to about a 2:1 ratio.

The additive may be directly added to the monomer stream by direct injection to pump suction or by quill during the distillation, purification, and/or fractionation process. Alternatively, the additive may be added to the equipment used for distillation, purification, and/or fractionation purposes. In one non-limiting embodiment, the additive may be injected into the feed, the reflux, and/or the boiler loop on a continuous basis, or the additive may be injected about every 0.5 hour to about 1 hour in an alternative embodiment. The effective amount of the additive may range from about 0.01 ppm independently to about 10,000 ppm, alternatively from about 1 ppm independently to about 5000 ppm, or from about 1 ppm independently to about 1200 ppm.

The invention will be further described with respect to the following Examples which are not meant to limit the invention, but rather to further illustrate the various embodiments.

EXAMPLE 1

A gum test was performed where the standard heat induced gum test was used. 300 ppm of each polymerization retarder was tested in a 25% fresh styrene sample in toluene. The samples were heated to 100° C. for 4 hours. After heating, the samples were cooled to room temperature and evaporated in a hot nitrogen environment. The polymer reduction percentage was determined by the following equation:

Polymer Reduction(%)=[(blank−gum)/blank]*100.

The polymerization retarders reduced the polymer formation by at least 99%, as shown in the results in Table 1 below.

TABLE 1

Gum Test with Different Quinone Derivatives

| Samples | Gum (mg) | Polymer Reduction (%) |
|---------|----------|----------------------|
| Blank   | 800      | 0                    |
| 2, 6 BQ | 2.3      | 99.7                 |
| 2, 5 BQ | 1.5      | 99.8                 |
| 3, 5 BQ | 2.4      | 99.7                 |

EXAMPLE 2

Kinetic testing was performed on uninhibited styrene samples in the presence of the polymerization retarders noted in FIG. 1. The graph in FIG. 1 illustrates the comparison of percent polymer formation in a certain period of time with/without the presence of individual polymerization retarder. A 20 mL fresh prepared styrene monomer contained 375 ppm polymerization retarder was degassed and heated at 100° C. A 20 mL fresh prepared styrene monomer without any retarder was used blank. At certain period of time, the sample was removed from the heat. The sample was cooled down. The styrene polymers were precipitated by adding 30 mL of methanol. The polymer was filtered, dried and weighted. The percent polymer formation was calculated based on the equation below:

% polymer=styrene polymer/weight of initial weight of styrene×100

As shown in FIG. 1, the benzoquinones slowed the polymer formation as compared to the uninhibited styrene without benzoquinone added thereto. 3,5 BQ slowed the formation of the styrene polymers for the longest amount of time, which was about 4 hours.

EXAMPLE 3

Figure 2:
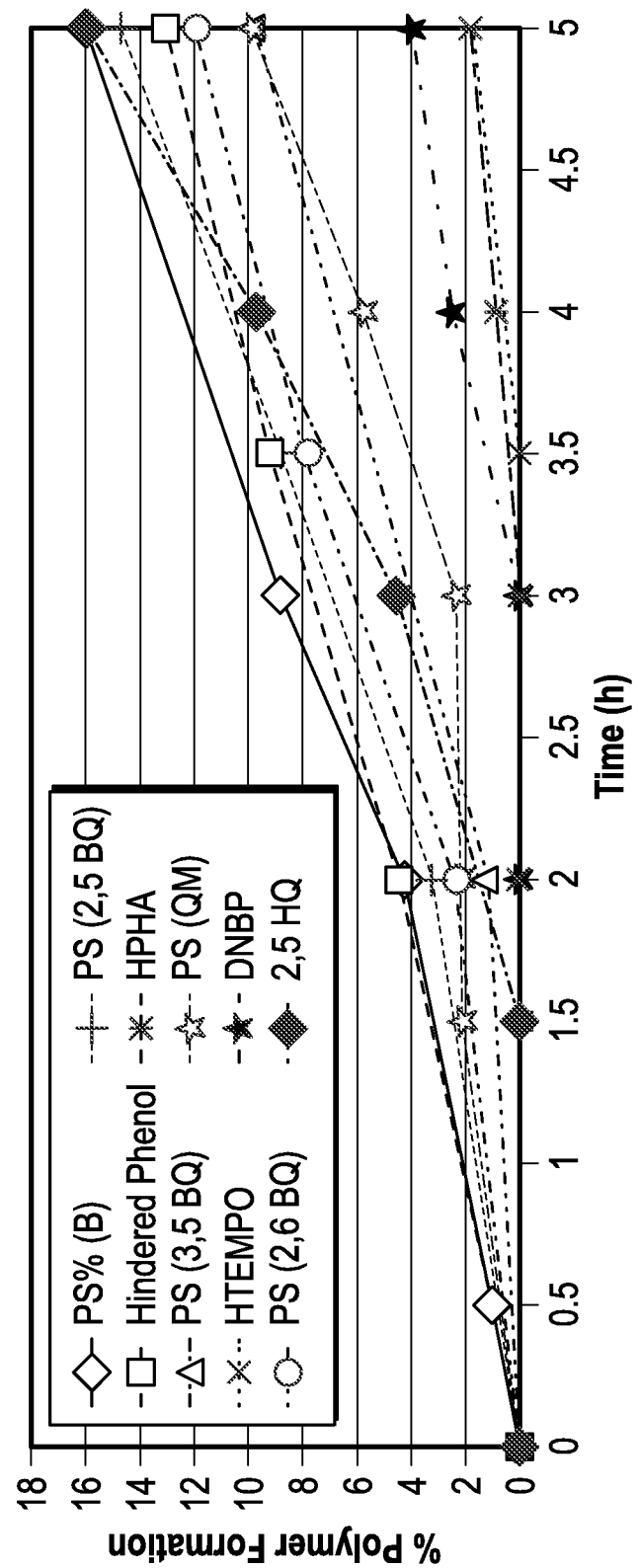
FIG. 2 is another graph illustrating the percent polymer formation compared to the amount of time each polymerization retarder is present.

Kinetic testing was performed on uninhibited styrene samples in the presence of the polymerization retarders and inhibitors noted in FIG. 2. The graph in FIG. 2 illustrates the percent polymer formation compared to the amount of time each polymerization retarder was present. A 20 mL fresh styrene samples with 50 ppm retarders were degassed and heated to 100° C. At the certain time period, the sample was removed from the heat and cooled down. The styrene polymers was precipitated by adding 30 mL methanol. The percent polymer formation was calculated based on the same formula as noted in EXAMPLE 2. As shown in FIG. 2, the benzoquinones slowed the polymer formation as compared to the uninhibited styrene without the polymerization retarder added thereto.

In the foregoing specification, the invention has been described with reference to specific embodiments thereof, and has been described as effective in providing methods and compositions for at least partially inhibiting the polymerization of monomers by introducing to the monomers an effective amount of an additive. However, it will be evident that various modifications and changes can be made thereto without departing from the broader spirit or scope of the invention as set forth in the appended claims. Accordingly, the specification is to be regarded in an illustrative rather than a restrictive sense. For example, specific monomers, polymerization retarders, polymerization inhibitors, and solvents falling within the claimed parameters, and specific proportions or dosages, but not specifically identified or tried in a particular composition or method, are expected to be within the scope of this invention.

The present invention may suitably comprise, consist or consist essentially of the elements disclosed and may be practiced in the absence of an element not disclosed. For instance, the method may consist of or consist essentially of inhibiting the polymerization of monomers by introducing to the monomers an effective amount of an additive, where the additive includes at least a first compound having the formula of compound (A). The composition may be a treated monomer stream consisting of or consisting essentially of polymerizable monomers, and an additive therein for at least partially inhibiting the polymerization of the monomers within the monomer stream, where the additive includes at least a first compound of the general formula (A).

The words "comprising" and "comprises" as used throughout the claims, are to be interpreted to mean "including but not limited to" and "includes but not limited to", respectively.

What is claimed is:

1. A treated monomer stream comprising:
polymerizable monomers selected from the group consisting of a styrene, a butadiene, an isoprene, acrylonitrile, vinyl acetate, and combinations thereof; and
an additive therein for reducing the rate of polymerization of the polymerizable monomers within the monomer stream; wherein the additive consists of:
a first compound of the general formula:

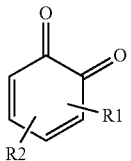

wherein R1 and R2 are selected from the group consisting of an alkyl group, an aryl group, an alkyl group having a heteroatom, and an aryl group having a heteroatom; wherein the heteroatom is selected from the group consisting of sulfur, nitrogen, and oxygen; and wherein R1 is the same or different from R2; and a second compound selected from the group consisting of 2,6-di-tert-butyl-1,4-benzoquinone (2,6 BQ); 2,5-di-tert-butyl-1,4-benzoquinone (2,5 BQ); 4-sec-butyl-2,6-di-tert-butylphenol; and combinations thereof; wherein the ratio between the first compound and the second compound is based on weight and ranges from about a 1:1 ratio to about a 1:5 ratio.

2. The treated monomer stream of claim 1, wherein the first compound is 3,5-di-tert-butyl-1,2-benzoquinone (3,5 BQ), 3,5-di-methyl-1,2 benzoquinone, 3,6-di-tert-butyl-1,2-benzoquinone and combinations thereof.

3. The treated monomer stream of claim 1, wherein the effective amount of the additive ranges from about 0.01 ppm to about 10,000 ppm.

* * * * *